(12) United States Patent
Stolen et al.

(10) Patent No.: US 10,502,747 B2
(45) Date of Patent: *Dec. 10, 2019

(54) SYSTEMS AND METHODS USING BIOMARKER PANEL DATA

(71) Applicants: CARDIAC PACEMAKERS, INC., St. Paul, MN (US); MUSC Foundation for Research Development, Charleston, SC (US)

(72) Inventors: Craig M. Stolen, New Brighton, MN (US); Timothy E. Meyer, North Oaks, MN (US); Milan Seth, Minneapolis, MN (US); Francis G. Spinale, Blythewood, SC (US); Nicholas David Wold, Arden Hills, MN (US)

(73) Assignees: Cardiac Pacemakers, Inc., St. Paul, MN (US); MUSC Foundation for Research Development, Charleston, SC (US)

( * ) Notice: Subject to any disclaimer, the term of this patent is extended or adjusted under 35 U.S.C. 154(b) by 300 days.

This patent is subject to a terminal disclaimer.

(21) Appl. No.: 13/756,129

(22) Filed: Jan. 31, 2013

(65) Prior Publication Data

US 2013/0237439 A1 Sep. 12, 2013

Related U.S. Application Data

(60) Provisional application No. 61/593,037, filed on Jan. 31, 2012.

(51) Int. Cl.
| | |
|---|---|
| *G01N 33/68* | (2006.01) |
| *A61B 5/00* | (2006.01) |
| *A61B 5/07* | (2006.01) |
| *A61B 5/145* | (2006.01) |
| *A61N 1/362* | (2006.01) |
| *A61N 1/39* | (2006.01) |
| *A61N 1/365* | (2006.01) |

(52) U.S. Cl.
CPC ....... *G01N 33/6893* (2013.01); *A61B 5/0031* (2013.01); *A61B 5/076* (2013.01); *A61B 5/14503* (2013.01); *A61B 5/14546* (2013.01); *A61B 5/686* (2013.01); *A61N 1/3627* (2013.01); *A61N 1/36557* (2013.01); *A61N 1/3956* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,562,841 A | 1/1986 | Brockway et al. | |
| 7,764,995 B2 | 7/2010 | Girouard et al. | |
| 7,809,441 B2 | 10/2010 | Kane et al. | |
| 7,907,997 B2 | 3/2011 | Stahmann et al. | |
| 8,602,996 B2 | 12/2013 | Thakur et al. | |
| 9,227,071 B2 | 1/2016 | Stolen et al. | |
| 9,457,184 B2 | 10/2016 | Scharmer | |
| 2003/0109420 A1 | 6/2003 | Valkirs et al. | |
| 2005/0004476 A1 | 1/2005 | Payvar et al. | |
| 2006/0094064 A1 | 5/2006 | Ray et al. | |
| 2006/0111746 A1 | 5/2006 | Foreman et al. | |
| 2007/0141627 A1 | 6/2007 | Behrens et al. | |
| 2007/0178605 A1 | 8/2007 | Mor et al. | |
| 2007/0270675 A1 | 11/2007 | Kane et al. | |
| 2008/0044843 A1 | 2/2008 | Perlee et al. | |
| 2008/0058642 A1 | 3/2008 | Gould et al. | |
| 2008/0288009 A1 | 11/2008 | Kim et al. | |
| 2010/0015643 A1 | 1/2010 | Tei et al. | |
| 2010/0204744 A1 | 8/2010 | Shuros et al. | |
| 2010/0233727 A1 | 9/2010 | Dudley, Jr. et al. | |
| 2011/0009861 A1 | 1/2011 | Mukherjee et al. | |
| 2011/0071583 A1 | 3/2011 | Muntendam | |
| 2011/0144205 A1 | 6/2011 | Damy et al. | |
| 2011/0295084 A1 | 12/2011 | Thakur et al. | |
| 2013/0046196 A1 | 2/2013 | Stolen et al. | |

(Continued)

FOREIGN PATENT DOCUMENTS

| | | |
|---|---|---|
| CN | 104159638 | 11/2014 |
| EP | 2726147 | 5/2014 |

(Continued)

OTHER PUBLICATIONS

Mueller et al., "Increased Plasma Concentrations of Soluble ST2 are Predictive for 1-Year Mortality in Patients with Acute Destabilized Heart Failure," Clin. Chem. 2008, 54:752-756.*

Gras et al., "Optimization of AV and VV Delays in the Real-World CRT Patient Population: An International Survey on Current Clinical Practice", Pacing Clin. Electrophysiol. 2009, 32:S236-S239.*

Tolosana et al., "Plasma tissue inhibitor of matrix metalloproteinase-1 (TIMP-1): an independent predictor of poor response to cardiac resynchronization therapy," Eur. J. Heart Fail. 2010, 12:492-498.*

(Continued)

*Primary Examiner* — Kaijiang Zhang
(74) *Attorney, Agent, or Firm* — Pauly, DeVries Smith & Deffner LLC

(57) ABSTRACT

Embodiments of the disclosure are related to systems and methods for utilizing biomarker panel data with respect to medical devices and methods, amongst other things. In an embodiment, the disclosure can include a method of predicting the likelihood of response to CRT therapy. The method can include quantifying levels of one or more biomarkers in a biological sample of a patient, analyzing the quantified levels to determine response to CRT therapy, wherein a panel of biomarkers includes at least two selected from the group consisting of CRP, SGP-130, sIL-2R, sTNFR-II, IFNg, BNP, sST2, MMP-2, MMP-9, TIMP-1, TIMP-2, TIMP-4. Other embodiments are also included herein.

11 Claims, 7 Drawing Sheets

(56) References Cited

U.S. PATENT DOCUMENTS

| | | | |
|---|---|---|---|
| 2014/0031641 | A1 | 1/2014 | Thakur et al. |
| 2017/0146552 | A1 | 5/2017 | Snider et al. |

FOREIGN PATENT DOCUMENTS

| | | |
|---|---|---|
| EP | 2809392 | 9/2016 |
| EP | 2809393 | 11/2016 |
| EP | 2726147 | 7/2017 |
| JP | 2006030183 | 2/2006 |
| JP | 2007503882 | 3/2007 |
| JP | 2008534196 | 8/2008 |
| JP | 2009537247 | 10/2009 |
| JP | 2009538634 | 11/2009 |
| JP | 2011502696 | 1/2011 |
| JP | 2014521402 | 8/2014 |
| WO | 2005020797 | 3/2005 |
| WO | 2006106132 | 10/2006 |
| WO | 2007092330 | 8/2007 |
| WO | WO 2008008809 A2 * | 1/2008 |
| WO | 2009064400 | 5/2009 |
| WO | 2009092381 | 7/2009 |
| WO | 2009100907 | 8/2009 |
| WO | 2011024107 | 3/2011 |
| WO | 2013003604 | 1/2013 |
| WO | 2013116544 | 8/2013 |
| WO | 2013116547 | 8/2013 |

OTHER PUBLICATIONS

"International Search Report and Written Opinion", for PCT Application No. PCT/US2013/024185, dated May 17, 2013, 17 pages.

Ellenbogen, Kenneth A. et al., "Primary Results From the SmartDelay Determined AV Optimization: A Comparison to Other AV Delay Methods Used in Cardiac Resynchronization Therapy (SMART-AV) Trial", *Circulation* 2010; 122; 2660-2668; originally published online Nov. 15, 2010 (19 Pages).

Elmenyar, A., "Cytokines and Myocardial Dysfunction: State of the Art", *Journal of Cardiac Failure*, vol. 14, No. 1, Feb. 1, 2008, pp. 61-74.

Glick, Aaron et al., "Neurohormonal and inflammatory markers as predictors of short-term outcome in patients with heart failure and cardiac resynchronization therapy", *IMAJ*, Jun. 1, 2006, pp. 391-394.

Kubanek, M. et al., "Decrease in plasma B-type natriuretic peptide early after initiation of cardiac resynchronization therapy predicts clinical improvement at 12 months", *European Journal of Heart Failure, Elsevier*, Amsterdam, NL, vol. 8, No. 8, Dec. 1, 2006, pp. 832-840.

Marin, Francisco et al., "Influence of cardiac resynchronization therapy on indices of inflammation, the prothrombotic state and tissue remodeling in systolic heart failure: A pilot study", *Thrombosis Research*, vol. 128, No. 4, Oct. 1, 2011 pp. 391-394.

Theodorakis, George et al., "Anti-inflammatory effects of cardiac resynchronization therapy in patients with chronic heart failure", *PACE*, Mar. 1, 2006, pp. 255-261.

Communication Pursuant to Rules 161(1) and 162 EPC, for European Patent Application No. 13707474.6 dated Sep. 9, 2014 (2 pages).

"International Preliminary Report on Patentability", for PCT/US2013/024185 dated Aug. 14, 2014 (10 pages).

"Communication Pursuant to Article 94(3) EPC," for European Patent Application No. 12733574.3 dated Feb. 25, 2015 (5 pages).

"Communication Pursuant to Article 94(3) EPC," for European Patent Application No. 13707474.6 dated May 19, 2015 (5 pages).

"Communication Pursuant to Rules 161(1) and 162 EPC," for European Patent Application No. 12733574.3 dated Mar. 28, 2014 (2 pages).

"International Preliminary Report on Patentability," for PCT/US2012/044669 dated Jan. 16, 2014 (8 pages).

"International Search Report and Written Opinion," for PCT/US20121044669, dated Sep. 19, 2012, (13 pages).

"Non-Final Office Action," for Chinese Patent Application No. 201380007531.7 dated Jun. 2, 2015 (23 pages) with English translation.

"Non-Final Office Action," for U.S. Appl. No. 14/041,682 dated May 4, 2015 (10 pages).

"Notice of Allowance," for U.S. Appl. No. 14/041,682 dated Aug. 17, 2015 (5 pages).

"Office Action," for Japanese Patent Application No. 2014-555712 dated Aug. 18, 2015 (6 pages) with English translation.

"Response Non-Final Office Action," for U.S. Appl. No. 14/041,682 dated May 4, 2015 and filed with the USPTO Jul. 20, 2015 (9 pages).

"Response to Communication Pursuant to Article 94(3) EPC," for European Patent Application No. 12733574.3 dated Feb. 25, 2015 and filed with the EPO Apr. 13, 2015 (10 pages).

"Response to Communication Pursuant to Rules 161(1) and 162 EPC," for European Patent Application No. 12733574.3 dated Mar. 28, 2014 and filed with the EPO on Oct. 6, 2014 (9 pages).

Theodorakis, George N. "Anti-Inflammatory Effects of Cardiac Resynchronization Therapy in Patients with Chronic Heart Failure," PACE, U.S., Blackwell Publishing Inc., Mar. 2006, vol. 29, pp. 255-261.

"Second Office Action," for Chinese Patent Application No. 201380007531.7 dated Feb. 5, 2016 (24 pages).

"Communication Pursuant to Article 94(3) EPC," for European Application No. 13703982.2 dated May 19, 2015 (5 pages).

"Decision of Rejection," for Japanese Patent Application No. 2014-555712 dated Mar. 15, 2016 (5 pages).

Felkin, Leanne E. et al., "A Quantitative Gene Expression Profile of Matrix Metalloproteinases (MMPS) and their Inhibitors (TIMPS) in the Myocardium of Patients With Deteriorating Heart Failure Requiring Left Ventricular Assist Device Support," J Heart Lung Transplant 2006;25:1413-9 (8 pages).

"Final Office Action," for U.S. Appl. No. 13/756,135 dated Jun. 30, 2014 (9 pages).

"Final Office Action," for U.S. Appl. No. 13/756,135 dated May 26, 2016 (32 pages).

"First Office Action," for Chinese Patent Application No. 201380007515.8 dated Mar. 27, 2015 (13 pages) with English translation.

Ford, Emily S. et al., "Traditional risk factors and D-dimer predict incident cardiovascular disease events in chronic HIV infection," AIDS, Jun. 19, 2010; 24 (10): 1509-1517.

"International Preliminary Report on Patentability," for PCT/US2013/024189 dated Aug. 14, 2014 (10 pages).

"International Search Report and Written Opinion," for PCT Application No. PCT/US2013/024189, dated May 17, 2013, (17 pages).

Januzzi, James L. et al., "Importance of biomarkers for long-term mortality prediction in acutely dyspneic patients," Clinical Chemistry 56:12; 1814-1821 (2010).

"Non-Final Office Action," for U.S. Appl. No. 13/756,135 dated Feb. 12, 2016 (33 pages).

"Non-Final Office Action," for Japanese Patent Application No. 2014-555713 dated Aug. 18, 2015 (6 pages) with English translation.

"Non-Final Office Action," for U.S. Appl. No. 13/756,135 dated Aug. 26, 2015 (26 pages).

"Non-Final Office Action," from U.S. Appl. No. 13/756,135 dated Oct. 16, 2013 (17 pages).

"Notice of Allowance," for U.S. Appl. No. 13/536,526 dated Nov. 20, 2015 (15 pages).

Pascual-Figal, Domingo A. et al., "Soluble ST2 for Predicting Sudden Cardiac Death in Patients with Chronic Heart Failure and Left Ventricular Systolic Dysfunction," Journal of the American College of Cardiology vol. 54, No. 23, 2009.

"Response to Communication Pursuant to Article 94(3) EPC," for European Application No. 13703982.2 dated May 19, 2015 and filed with the EPO Sep. 11, 2015 (15 pages).

"Response to Non-Final Office Action," for U.S. Appl. No. 13/756,135 dated Aug. 26, 2015 and filed with the USPTO Nov. 17, 2015 (9 pages).

(56) References Cited

OTHER PUBLICATIONS

"Response to Non-Final Office Action," for U.S. Appl. No. 13/756,135 dated Feb. 12, 2016 and file with the USPTO May 5, 2016 (15 pages).
Scott, Paul A. et al., "Defining potential to benefit from implantable cardioverter defibrillator therapy: the role of biomarkers," Europace (2011) 13, 1419-1427 (9 pages).
"Second Office Action," for Chinese Patent Application No. 201380007515.8 dated Nov. 4, 2015 (10 pages) including English translation.
"Third Office Action," for Chinese Patent Application No. 201380007515.8 dated Jan. 14, 2016, with English translation (7 pages).
"Third Office Action," for Chinese Patent Application No. 201380007531.7 dated Aug. 11, 2016 (14 pages) with English translation.
Young, James B. et al., "Combined Cardiac Resynchronization and Implantable Cardioversion Defibrillation in Advanced Heart Failure—The MIRACLE ICD Trial," JAMA, vol. 289(20), May 28, 2003., 2685-94.
"Decision of Rejection," for Chinese Patent Application No. 201380007531.7 dated Aug. 4, 2017 (7 pages).
"Response to Appeal Decision," for U.S. Appl. No. 13/756,135, filed with the USPTO May 5, 2018 (7 pages) in response to Appeal Decision dated Mar. 5, 2018.
Final Office Action for U.S. Appl. No. 13/756,135 dated Dec. 26, 2018 (43 pages).
Response to Final Rejection dated Dec. 26, 2018, for U.S. Appl. No. 13/756,135 submitted via EFS-Web on Feb. 5, 2019, 19 pages.
Response to Non-Final Rejection dated Oct. 11, 2018, for U.S. Appl. No. 13/756,135 submitted via EFS-Web on Nov. 30, 2018, 20 pages.
Barold, S. S. et al., "First-degree atrioventricular block," J Interv Card Electrophysiol (2006) 17:139-152 (14 pages).
Jacob, Sony et al., "Serial Changes in Specific Biomarkers Reflect Cardiac Resynchronization Therapy Response: Results From the SMART-AV Trial," ABSTRACT ONLY from the American Heart Association's 2014 Scientific Sessions and Resuscitation Science Symposium, Circulation, (Nov. 25, 2014) vol. 130, No. Suppl. 2 (6 pages).
Non-Final Office Action for U.S. Appl. No. 13/756,135 dated Oct. 11, 2018 (52 pages).
Stein, Kenneth M. et al., "SmartDelay Determined AV Optimization: A Comparison of AV Delay Methods Used in Cardiac Resynchronization Therapy (SMART-AV): Rationale and Design," Pacing and Clinical Electrophysiology, 2010 vol. 33(1) pp. 54-63 (10 pages).

\* cited by examiner

SYSTEMS AND METHODS USING BIOMARKER PANEL DATA

This application claims the benefit of U.S. Provisional Application No. 61/593,037, filed Jan. 31, 2012, the content of which is herein incorporated by reference in its entirety.

TECHNICAL FIELD

This disclosure relates generally to medical devices and methods, and more particularly, to systems and methods for utilizing biomarker panel data with respect to medical devices and methods, amongst other things.

BACKGROUND OF THE INVENTION

Implantable medical devices (IMDs) are commonly used to provide treatment to patients. Some types of implantable medical devices deliver electrical stimuli to a target tissue via a lead wire ("stimulation lead") or catheter having one or more electrodes disposed in or about the target tissue. In the context of cardiac rhythm management devices, the electrical stimuli can be delivered in the form of pacing pulses to pace the heart and/or relatively high energy defibrillation shocks or cardioversion shocks to terminate arrhythmias.

The American College of Cardiology/American Heart Association Guidelines for the Evaluation and Management of Chronic Heart Failure in the Adult defines heart failure as a "complex clinical syndrome that can result from any structural or functional cardiac disorder that impairs the ability of the ventricle to fill with or eject blood". Heart failure has various adverse hemodynamic and circulatory consequences. Signs and symptoms of heart failure include systemic and pulmonary fluid accumulation, reduced activity levels and exercise tolerance, and poor kidney and cerebral/cognitive function, amongst others. Over time, patients with heart failure typically experience further declines in cardiac pump function which is accompanied by increased fluid accumulation, continued decline in activity/exercise tolerance, further decline in kidney and cerebral/cognitive function.

Cardiac resynchronization therapy (CRT) is used to treat the delay in ventricular contractions of the heart that occur in some people with advanced heart failure. A delay between the contraction of the right and left ventricles often occurs with heart failure, leading to biomechanically inefficient heart contractions and reduced cardiac output. Cardiac resynchronization therapy aims to address this problem through stimulation of multiple chambers of the heart in order to resynchronize contraction of the right and left ventricles.

Biomarkers, or biological markers, are substances that can be used as an indicator of a biological state. Biomarkers can include small molecules, proteins, nucleic acids, carbohydrates, lipids, and combinations thereof.

SUMMARY OF THE INVENTION

Embodiments of the disclosure are related to systems and methods for utilizing biomarker panel data and related medical devices and methods, amongst other things. An embodiment can include a method of predicting the likelihood of response to CRT therapy. The method can include quantifying levels of one or more of a panel of biomarkers in a biological sample of a patient, analyzing the quantified levels to determine likelihood of response to CRT therapy, wherein the panel of biomarkers includes at least two selected from the group consisting of CRP, SGP-130, sIL-2R, sTNFR-II, IFNg, BNP, sST2, MMP-2, MMP-9, TIMP-1, TIMP-2, TIMP-4. In some embodiments, the method can include quantifying levels of one or more of a panel of biomarkers in a biological sample of a patient, and using the quantified levels to place the patient into one of a set of categories, the set of categories including CRT therapy responders, wherein the panel of biomarkers includes at least two selected from the group consisting of CRP, SGP-130, sIL-2R, sTNFR-II, IFN-γ, BNP, sST2, MMP-2, MMP-9, TIMP-1, TIMP-2, TIMP-4.

An embodiment can include a method of identifying patients that are unlikely to respond to CRT therapy. The method can include quantifying levels of one or more of a panel of biomarkers in a biological sample of a patient, and analyzing the quantified levels to determine likelihood of response to CRT therapy, wherein the panel of biomarkers includes at least two selected from the group consisting of CRP, SGP-130, sIL-2R, sTNFR-II, IFNg, BNP, sST2, MMP-2, MMP-9, TIMP-1, TIMP-2, TIMP-4.

An embodiment can include a method of determining prognosis of a patient receiving CRT therapy. The method can include selecting a patient that is receiving CRT therapy, quantifying levels of one or more of a panel of biomarkers in a biological sample of the patient, and analyzing the quantified levels to determine prognosis, wherein the panel of biomarkers includes at least two selected from the group consisting of CRP, SGP-130, sIL-2R, sTNFR-II, IFNg, BNP, sST2, MMP-2, MMP-9, TIMP-1, TIMP-2, TIMP-4.

An embodiment can include a method of treating a patient. The method can include quantifying levels of one or more of a panel of biomarkers in a biological sample of the patient, analyzing the quantified levels, and adjusting therapy for the patient based at least in part on the analysis results, wherein the panel of biomarkers includes at least two selected from the group consisting of CRP, SGP-130, sIL-2R, sTNFR-II, IFNg, BNP, sST2, MMP-2, MMP-9, TIMP-1, TIMP-2, TIMP-4. In some embodiments, the method can include selecting a patient that is receiving CRT therapy, quantifying levels of one or more of a panel of biomarkers in a biological sample of the patient, analyzing the quantified levels to determine an expected response to CRT therapy, comparing the expected response to CRT therapy to the patient's actual response to CRT therapy, and adjusting parameters of the CRT therapy if the patient's actual response to CRT therapy is worse than the expected response to CRT therapy, wherein the panel of biomarkers includes at least two selected from the group consisting of CRP, SGP-130, sIL-2R, sTNFR-II, IFNg, BNP, sST2, MMP-2, MMP-9, TIMP-1, TIMP-2, TIMP-4.

An embodiment can include a method of monitoring a patient receiving CRT therapy. The method can include quantifying levels of one or more of a panel of biomarkers in a biological sample of the patient, and analyzing the quantified levels to determine status. In some embodiments the method can include quantifying levels of one or more of a panel of biomarkers in a biological sample of the patient, and analyzing the change in quantified levels over time to perform one or more selected from the group consisting of analyzing response to therapy changes and monitoring disease progression.

An embodiment can include an assay kit including probes to quantify levels of one or more of a panel of biomarkers in a biological sample of a patient, wherein the panel of biomarkers includes at least two selected from the group consisting of CRP, SGP-130, sIL-2R, sTNFR-II, IFNg, BNP, sST2, MMP-2, MMP-9, TIMP-1, TIMP-2, TIMP-4.

This summary is an overview of some of the teachings of the present disclosure and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The disclosure may be more completely understood in connection with the following drawings, in which.

Figure 1:
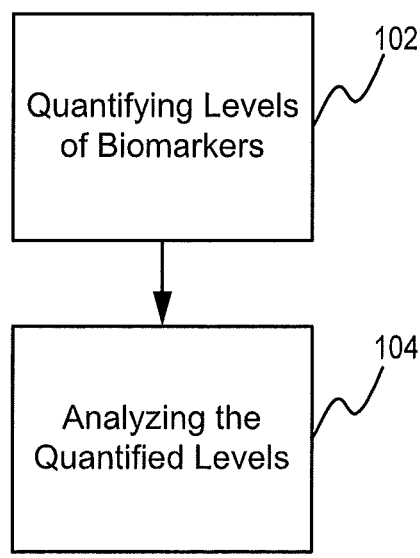
FIG. 1 is a flow chart of some steps of methods in accordance with various embodiments herein.

While the disclosure is susceptible to various modifications and alternative forms, specifics thereof have been shown by way of example and drawings, and will be described in detail. It should be understood, however, that the disclosure is not limited to the particular embodiments described. On the contrary, the intention is to cover modifications, equivalents, and alternatives falling within the spirit and scope of the disclosure.

DETAILED DESCRIPTION

Cardiac resynchronization therapy (CRT) is a recognized device driven therapy for heart failure (HF) secondary to severe LV dysfunction. However, outcomes in these HF patients following CRT can be variable as defined by clinical course and/or LV functional improvement. Studies have identified that there is a proportion of patients with cardiac dysfunction that do not respond to cardiac resynchronization therapy (CRT) as would be expected, and as such, there is a subset of patients that receive CRT but the progression to HF (heart failure) and risk of MACE (major adverse cardiovascular events including but not limited to hospitalization for heart failure, myocardial infarction or cardiogenic shock, stroke or thromboembolic event, and death) is unaffected. At present, there is no validated approach to predict those HF patients that would yield a functional benefit from CRT. Moreover, early differentiation of those patients that will not optimally respond to CRT remains a clinical challenge.

In various embodiments, a plasma biomarker panel is included that predicts (including prior to CRT implant) those HF patients that would demonstrate a functional response to CRT. In various embodiments, a biomarker profile is included that can be used to differentiate a functional response in HF patients following CRT placement.

In some embodiments, a peripheral, non-invasive diagnostic test quantifying a specific combination of biomarkers, taken at the time of CRT evaluation, but prior to CRT placement, can predict those patients that will have HF and MACE risk reduced, or conversely identify those patients that will not have these indices of cardiovascular risk effectively reduced.

In some embodiments, prediction algorithms, and/or devices executing the same, can predict and/or stratify those patients that will demonstrate improved cardiac performance following CRT and thereby slow the progression of HF and reduce the risk of MACE.

In some embodiments, a specific test of a biological sample (such as a blood test) for a specific set of biomarkers can be used to assess the response of patients after placement of CRT. Such embodiments can be advantageous because identifying the relative response to CRT, particularly early following CRT placement can be difficult and often requires complex imaging and functional studies. As such, in accordance with some embodiments herein, a specific peripheral, diagnostic test can provide diagnostic information on those patients that are responding to CRT, and inversely identify those patients that are not responding to CRT as would be predicted. Such embodiments can serve to provide early warning information that can then be used to initiate early and more aggressive workup of these patients including, but not limited to, reprogramming a CRT (cardiac resynchronization therapy) device, altering medications, performing additional imaging and invasive functional studies.

It will be understood then that some embodiments herein include systems and methods for utilizing biomarker panel data in order to perform various tasks such as predicting response to CRT therapy, identifying patients that are unlikely to respond to CRT therapy, determine the prognosis of patients received CRT therapy, treat patients with CRT therapy, adjust CRT therapy treatment, and monitor patients receiving CRT therapy, amongst others. Also included herein are biomarker assay kits.

As used herein, the term "biomarker" shall include measurable substances that can be used as an indicator of a biological state including, without limitation, small molecules, proteins, nucleic acids, carbohydrates, lipids, and combinations thereof. It will be appreciated that reference to specific biomarkers herein shall include reference to precursors, proforms, isoforms, mature form variants, and degraded forms thereof including but not limited to metabolites thereof unless the context dictates otherwise.

It will be appreciated that many different types of biomarkers can be utilized in embodiments herein. Biomarkers used in various embodiments herein can include, but are not limited to adiponectin, adrenomedullin, midregion proadrenomedullin, angiotensin II, apelin, BNP, BNP1-32, NTproBNP1-76, caspase-3, connexin-43, copeptin, C-reactive protein (CRP), dihydropyridine receptor, epidermal growth factor (EGF), endoglin, endothelin, endothelin-1, big endothelin, eotaxin, fibroblast growth factor-2 (FGF-2), fibronectin, Flt-3 ligand, fractalkine, galectin 3 (Gal-3), G-CSF, GDF-15, GM-CSF, GRO, ICTP, IFNa2, IFN-gamma, IGF-1, IL-1, IL-1a, IL-1b, IL-1ra, IL-2, IL-3, IL-4, IL-5, IL-6, IL-7, IL-8, IL-9, IL-10, IL-12 (p40), IL-12 (p70), IL-13, IL-15, IL-17, IP-10, L-type calcium channel alpha subunit, MCP-1, MCP-3, MDC, MIP-1a, MIP-1b, miR-1, miR-21, miR-29, miR-30, miR-133, miR-208, miR-486, miR-760, MMP-1, MMP-2, MMP-3, MMP-7, MMP-8, MMP-9, MMP-12, MMP-13, MPO, osteopontin, PAI-I, PDGF-AA, PDGF-AB/BB, PIIINP, PINP, PRA-plasma rennin, RANTES, RNU 44, RNU 6B, sCD30, sCD40L, sEGFR, sE-selectin, sgp130, sICAM-I, sIL-1Rib, sIL-1RII, sIL-2Ra, sIL-4R, sIL-6R, sRAGE, ST2, sST2, sTNF RI, sTNF RII, sVCAM-I, sVEGFR1, sVEGFR2, sVEGFR3, TGFa, TGF bI, TGF bII, TGF bIII, TIMP-1, TIMP-2, TIMP-3, TIMP-4, TNFa, TNFb, TROPONIN-I, VEGF, ANP, NTproANP, midregion pro-ANP SERCA2a, ryanodine receptor, carboxy-terminal propeptide of procollagen type I (PICP), C-type natriuretic peptides (CNP, NTproCNP), aldosterone, epinephrine, arginine vasopressin (AVP), copeptin, urocortins I, II, III, Fas(APO-1), sFas, FasL, IL-18, oxidized low-density lipoproteins, myeloperoxidase, urine biopyrrins, urine and plasma isoprostanes, plasma malondialdehyde, carbonyl proteins, cardiac troponins I and T, myosin light-chain kinase I, heart fatty acid binding protein, creatine kinase MB fraction, ischemia modified albumin, osteoprotegerin, coenzyme Q10, sGp130, sTNFr-II, VAP-1, sVCAM-1, M-CSF, GM-CSF, and analogues thereof.

In some embodiments, biomarkers can include, but are not limited to, heart failure markers, inflammatory biomarkers, and/or remodeling biomarkers. In some embodiments, biomarkers can include, but are not limited to, biomarkers of inflammation, bioactive biomarkers, and/or proteolytic biomarkers.

It will be appreciated that a relatively diverse set of biomarkers can be relevant in terms of indicating inflammation. Specific biomarkers of inflammation in various embodiments herein can include, but are not limited to, CRP (C-reactive protein), SGP-130 (soluble glycoprotein 130), sIL-2R (soluble interleukin-2 receptor), sTNFR-II (soluble tumor necrosis factor receptor-II), IFN-γ (interferon gamma), sST2 (soluble suppressor of tumorigenicity-2), and fragments of any of these.

Bioactive biomarkers can include, but are not limited to, BNP (brain natriuretic peptide) and fragments thereof.

Proteolytic biomarkers can include, but are not limited to, MMPs and TIMPs. Matrix metalloproteinases (MMPs) are zinc-dependent endopeptidases. Synthesized as pro-enzymes, most MMPs are secreted before conversion to their active form. MMPs are capable of degrading extracellular matrix proteins in addition to processing a number of bioactive molecules. MMPs play an important role in breaking down components of the extracellular matrix (ECM). Specific MMPs for use as proteolytic biomarkers in various embodiments herein can include, but are not limited to, MMP-2; MMP-9; and fragments of any of these.

Tissue inhibitors of metalloproteinases (TIMPs) function by suppressing MMPs. Structurally, TIMPs contain two domains. The N-terminal domain binds to the active site of mature metalloproteases via a 1:1 non-covalent interaction, blocking access of substrates to the catalytic site. Specific TIMPs for use as proteolytic biomarkers in various embodiments herein can include, but are not limited to, TIMP-1, TIMP-2, TIMP-4; and fragments of any of these.

As used herein, the term "biomarker panel" shall refer to a set of biomarkers that can be used alone, together, or in subcombinations to indicate the status of a human subject with respect to a condition, status, or state of being of the human subject. The biomarkers within the panel of biomarkers can include those biomarkers discussed above. It will be appreciated that the specific identity of biomarkers within the panel and the number of distinct biomarkers within the panel can depend on the particular use to which the biomarker panel is put and the stringency that the results of panel must meet for the particular application.

In some embodiments, the panel includes at least two distinct biomarkers selected from CRP, SGP-130, sIL-2R, sTNFR-II, IFN-γ, BNP, sST2, MMP-2, MMP-9, TIMP-1, TIMP-2, and TIMP-4. In other embodiments, the panel includes at least three distinct biomarkers selected from CRP, SGP-130, sIL-2R, sTNFR-II, IFN-γ, BNP, sST2, MMP-2, MMP-9, TIMP-1, TIMP-2, and TIMP-4. In other embodiments, the panel includes at least four distinct biomarkers selected from CRP, SGP-130, sIL-2R, sTNFR-II, IFN-γ, BNP, sST2, MMP-2, MMP-9, TIMP-1, TIMP-2, and TIMP-4. In other embodiments, the panel includes at least five distinct biomarkers selected from CRP, SGP-130, sIL-2R, sTNFR-II, IFN-γ, BNP, sST2, MMP-2, MMP-9, TIMP-1, TIMP-2, and TIMP-4. In other embodiments, the panel includes at least six distinct biomarkers selected from CRP, SGP-130, sIL-2R, sTNFR-II, IFN-γ, BNP, sST2, MMP-2, MMP-9, TIMP-1, TIMP-2, and TIMP-4. In other embodiments, the panel includes at least seven distinct biomarkers selected from CRP, SGP-130, sIL-2R, sTNFR-II, IFN-γ, BNP, sST2, MMP-2, MMP-9, TIMP-1, TIMP-2, and TIMP-4. In other embodiments, the panel includes at least eight distinct biomarkers selected from CRP, SGP-130, sIL-2R, sTNFR-II, IFN-γ, BNP, sST2, MMP-2, MMP-9, TIMP-1, TIMP-2, and TIMP-4. In other embodiments, the panel includes at least nine distinct biomarkers selected from CRP, SGP-130, sIL-2R, sTNFR-II, IFN-γ, BNP, sST2, MMP-2, MMP-9, TIMP-1, TIMP-2, and TIMP-4. In other embodiments, the panel includes at least ten distinct biomarkers selected from CRP, SGP-130, sIL-2R, sTNFR-II, IFN-γ, BNP, sST2, MMP-2, MMP-9, TIMP-1, TIMP-2, and TIMP-4. In other embodiments, the panel includes at least eleven distinct biomarkers selected from CRP, SGP-130, sIL-2R, sTNFR-II, IFN-γ, BNP, sST2, MMP-2, MMP-9, TIMP-1, TIMP-2, and TIMP-4. In other embodiments, the panel CRP, SGP-130, sIL-2R, sTNFR-II, IFN-γ, BNP, sST2, MMP-2, MMP-9, TIMP-1, TIMP-2, and TIMP-4.

In some embodiments, the panel includes at least CRP, sST2, TIMP1, and TIMP2. In some embodiments, the panel includes at least CRP, BNP, and TNFR-II. In some embodiments, the panel includes at least CRP and BNP.

Because the biomarkers within a particular biomarker panel can include a heterogeneous group in terms of their underlying biological function, it will be appreciated that each biomarker included within a panel may have a different normal biological concentration and therefore each biomarker included within a panel may have a different concentration or concentration threshold that is significant for indicating a particular biological status. By way of example, normal serum concentrations of CRP (C-reactive protein) are different from normal serum concentrations of IL-2, and therefore analyzing their concentrations for application in the context of a panel of biomarkers may require accounting for different inherent magnitudes in concentrations between the two.

In some embodiments each individual biomarker is assessed according to normal values (or reference normal values) for that biomarker in patient populations. In other words, each individual biomarker can be assessed as either being higher than normal, normal, or lower than normal. In some embodiments, the reference normal levels are determined based on a group of healthy patients. In other embodiments, the group is patients with heart failure. In other embodiments, the group is patients with heart failure who have received CRT therapy devices. In still other embodiments, the group is made up of patients with heart failure who are responders to CRT therapy. In some embodiments, the group is made up of patients with heart failure who are not responders to CRT therapy.

Analysis of the biomarker panel can result in a positive result, a negative result, or an indeterminate result. In some embodiments, a positive biomarker panel result can be defined based on all of the biomarkers within the panel exceeding a threshold value. In other embodiments, a positive biomarker panel result can be defined based on a majority of the biomarkers within the panel exceeding a threshold value. In some embodiments, the threshold value can be a unique quantitative concentration for that particular biomarker. In other embodiments, the threshold value can be more qualitatively assessed as either normal or abnormal; or higher than normal, normal, or lower than normal.

Various embodiments herein can include quantifying levels of one or more of a panel of biomarkers in a biological sample of a patient. In some embodiments, quantifying levels can be conducted in vitro. In some embodiments, quantifying levels can be conducted in vivo. It will be appreciated that many different techniques exist for quantifying levels of biomarkers, depending of course on the nature of the specific biomarker. For example, in the context of identifying proteins or fragments thereof methods used can include, but are not limited to, ELISA (enzyme linked immunosorbent assay), western blotting, other types of electrophoretic analytic assays, immunohistochemical staining, affinity chromatography, mass spectrometry, and the like. In some embodiments, quantifying levels of one or more biomarkers can include quantifying levels of other compounds that would be indicative of those levels. By way of example, in the context of quantifying levels of a particular protein, detection of mRNA coding for the protein or precursors thereof can be used in order to quantify such levels. As such, in various embodiments, techniques can be used including northern blotting, RT-PCR (polymerase chain reaction), serial analysis of gene expression (SAGE), microarray assays, and the like. In the context of quantifying levels of particular proteins, other compounds that are indicative of those levels can include precursors, proforms, isoforms, mature form variants, and degraded forms including but not limited to metabolites thereof. It will be appreciated, however, that many other techniques exist that can be used to detect and/or quantify levels of biomarkers.

In some embodiments, other types of data can be used in conjunction with biomarker data for methods herein. By way of example, data can include but is not limited to, data regarding patient gender, ischemic or non-ischemic origin of heart failure, the presence or absence of left bundle branch block, QRS width (such as QRS width greater than or equal to 150 milliseconds), information on prior hospitalizations, left ventricular end-diastolic volume (LVEDV) (such as LVEDV greater than 125 mL/m$^2$, and left atrial volume (such as left atrial volume less than 40 mL/m$^2$). Use of such other types of data can include their use as binary variable or continuous variables where appropriate.

In some embodiments, the data used can include ST2, CRP, TIMP1, TIMP2, and one, two, three, or more of LVESV at baseline, age at baseline, sex, systolic blood pressure at baseline, QRS duration at baseline, PR interval at baseline, ischemic status at baseline, and ACE (angiotensin-converting enzyme inhibitors)/ARB (angiotensin II receptor blockers) use at baseline.

In some embodiments, the data used can include CRP, BNP, and one, two, three, or more of LVESV at baseline, age at baseline, sex, systolic blood pressure at baseline, presence of left bundle branch block at baseline, renal disease at baseline, ischemic status at baseline, and beta blocker use at baseline.

In some embodiments, the data used can include CRP, BNP, and one, two, three, or more of LVESV at baseline, age at baseline, sex, systolic blood pressure at baseline, QRS duration at baseline, PR interval at baseline, ischemic status at baseline, beta blocker use at baseline, and ACE/ARB use at baseline.

In some embodiments, the data used can include BNP, CRP, TNFR-II, and one, two, three, or more of LVESV at baseline, age at baseline, sex, systolic blood pressure at baseline, QRS duration at baseline, presence of left bundle branch block at baseline, ischemic status at baseline, and renal disease at baseline.

It will be appreciated that various samples can be used as the biological sample for testing in accordance with various embodiments herein. By way of example, samples can include, but are not limited to fluid samples (such as plasma, blood, blood serum, interstitial fluid, bodily filtrates, pleural fluid, lymph fluids, cerebrospinal fluid, mucus, peritoneal fluid, saliva, sweat, tears, urine, as well as other secretions, and the like) as well as tissue samples. In various embodiments, the method can further include the step of taking a biological sample of a patient.

In some embodiments herein, assay kits are included. Assay kits can include materials in order to facilitate quantifying levels of one or more of a panel of biomarkers in a biological sample of a patient. The specific components of an assay kit can depend on the technique used to quantify the biomarkers. By way of example, in some embodiments, the kit can include probes specific to one or more of a panel of biomarkers. In some embodiments, the kit can include probes exhibiting binding specificity to one or more of the panel of biomarkers. For example, in some embodiments, the kit can include antibodies exhibiting binding specificity to one or more of the panel of biomarkers. In some embodiments, the probes can be hybridization probes. In some embodiments, the probes themselves can include proteins, nucleic acids, and the like. In some embodiments, the probes can be attached to a substrate, such as probes attached to a coated glass slide or a gene chip.

Referring now to FIG. 1, in some embodiments, methods can include quantifying levels of one or more of a panel of biomarkers 102 in a biological sample of a patient. Quantification of the levels of the biomarkers in the panel can be performed in various ways, such as through the use of various techniques described above. In some embodiments, the quantification is an absolute value of the biomarker or panel of biomarkers. In some embodiments, the quantification is a relative value with respect to values for other markers, genomic or proteomic targets, or reference values. In still other embodiments, the quantification may reflect a change in levels over a time period (such as the time period between follow-up visits to a clinician or the time period between implant of a device and a follow-up visit to a clinician). In some embodiments, the change can be a change in absolute values. In other embodiments, the change can be measured relative to another piece of data regarding the patient, or change of specific biomarkers as measured relative to other biomarkers. In some embodiment, data regarding biomarker levels for a particular patient can be tracked over an extended period of time including measurements at a plurality (e.g., 2-100 or more) of time points and an overall profile of changes can be determined.

In some embodiments, measurements of biomarkers can be made prior to a patient receiving a CRT device. In other embodiments, measurements of biomarkers can be made after a patient has received a CRT device. In some embodiments, measurements of biomarkers can be made both prior to and after a patient receiving a CRT device.

Methods can also include analyzing the quantified levels 104. For example, method can include analyzing the quantified levels to determine response to CRT therapy. Analyzing the quantified levels can include various operations. In some embodiments, analyzing the quantified levels includes comparing quantified levels to reference normal levels to determine likelihood of response to CRT therapy. The reference normal levels can be determined in various ways. In some embodiments, the reference normal levels are determined based on a group of patients. In some embodiments, the group is made up of healthy patients. In other embodiments, the group is patients with heart failure. In other embodiments, the group is patients with heart failure who have received CRT therapy devices. In still other embodiments, the group is made up of patients with heart failure who are responders to CRT therapy. In some embodiments, the group is made up of patients with heart failure who are not responders to CRT therapy.

In some embodiments, analyzing the quantified levels includes calculating an aggregate score that represents the deviations of quantified levels from reference normal levels for the panel of biomarkers. Positive or negative deviations from reference normal levels can be indicative of likelihood of response to CRT therapy. In some embodiments, the specific degree of positive or negative deviations from reference normal levels can be indicative of likelihood of response to CRT therapy. In some embodiments, such as where reference normal levels are derived based on a group of patients with heart failure who are responders to CRT therapy, non-deviation from reference normal levels can be indicative of likelihood of response to CRT therapy. In some embodiments, analyzing the quantified levels comprises comparing quantified levels to threshold levels to determine likelihood of response to CRT therapy.

In some embodiments, methods can further include selecting a patient. In some embodiments, the patient can be selected on the basis of symptoms. For example, selecting the patient can be done on the basis of heart failure symptoms. In some embodiments, the symptoms can include subjective symptoms. In other embodiments, the symptoms can include objective symptoms. In still other embodiments, the symptoms can include combinations of subjective and objective symptoms. In some embodiments, selecting the patient can be based on what the patient is indicated for. By way of example, selecting the patient can be based on the patient being indicated for CRT therapy. In some embodiments, selecting the patient can be based on the patient suffering from heart failure, but not being indicated for CRT therapy.

In some embodiments, methods can further include determining whether the patient is unlikely to respond to CRT therapy.

Figure 2:
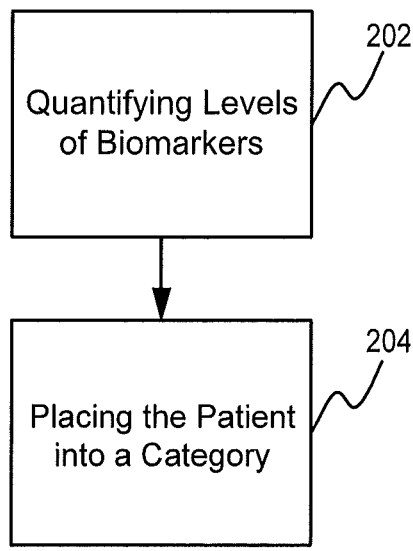
FIG. 2 is a flow chart of some steps of methods in accordance with various embodiments herein.

Some methods can include placing the patient into a category. For example, referring now to FIG. 2, methods can include quantifying levels of biomarkers 202 and placing the patient into a category 204. Some embodiments are directed to a method of predicting the likelihood of response to CRT therapy including quantifying levels of one or more of a panel of biomarkers in a biological sample of a patient and using the quantified levels to place the patient into one of a set of categories. Categories can include, but are not limited to, one or more of CRT therapy responders, non-responders, super responders (e.g., those predicted to respond to a larger than average degree amongst responders), negative responders, patients who would likely die regardless of CRT therapy, indeterminate responders, and the like. In some embodiments, the set of categories can include at least two categories. In some embodiments, the set of categories can include at least three categories. In some embodiments, the set of categories can include at least four categories. In some embodiments, the set of categories can include at least five categories.

In some embodiments, placement into a category can be based on the difference between quantified levels of one or more of the panel of biomarkers and reference normal levels for one or more of the panel of biomarkers. In some embodiments, different biomarkers receive equal weighting. In other embodiments, different biomarkers received different weighting.

In various embodiments, a method of identifying patients that are unlikely to respond to CRT therapy is included. The method can include quantifying levels of one or more of a panel of biomarkers in a biological sample of a patient and analyzing the quantified levels to determine likelihood of response to CRT therapy. In some embodiments, the method can further include the step of selecting the patient. By way of example, the method can include the step of selecting the patient based on the patient being indicated for CRT therapy. In some embodiments, the method can further include the step of selecting the patient based on the patient suffering from heart failure, but not being indicated for CRT therapy.

In some embodiments, a method of determining prognosis of a patient receiving CRT therapy is included. The method can include selecting a patient that is receiving CRT therapy, quantifying levels of one or more of a panel of biomarkers in a biological sample of the patient, and analyzing the quantified levels to determine prognosis. In some embodiments, prognosis can be determined based on comparing quantified levels to reference normal levels. As with the above, the reference normal levels can be determined in various ways. In some embodiments, the reference normal levels are determined based on a group of patients. In some embodiments, the group is made up of healthy patients. In other embodiments, the group is patients with heart failure. In some embodiments, the group is made up of patients with heart failure are responders to CRT therapy. In some embodiments, the group is made up of patients with heart failure who are not responders to CRT therapy. Also, as with the above, analyzing the quantified levels can include calculating an aggregate score that represents the deviations of quantified levels from reference normal levels for the panel of biomarkers in some embodiments. Positive or negative deviations from reference normal levels can be indicative of patient prognosis. In some embodiments, the specific degree of positive or negative deviations from reference normal levels can be indicative of patient prognosis. In some embodiments, non-deviation from reference normal levels can be indicative of likelihood of response to CRT therapy. In some embodiments, analyzing the quantified levels comprises comparing quantified levels to threshold levels to determine patient prognosis.

In some embodiments, data regarding biomarkers can be used as a companion diagnostic or theragnostic. One unique impact of such a theragnostic is that a peripheral sample can be easily obtained and analyzed and provide rapid turnaround information in order to guide the utilization of medical devices, and thereby provide a significant improvement over current diagnostics in that it will provide a prediction of CRT response and responsiveness, and thereby can improve medical resource utilization.

Figure 3:
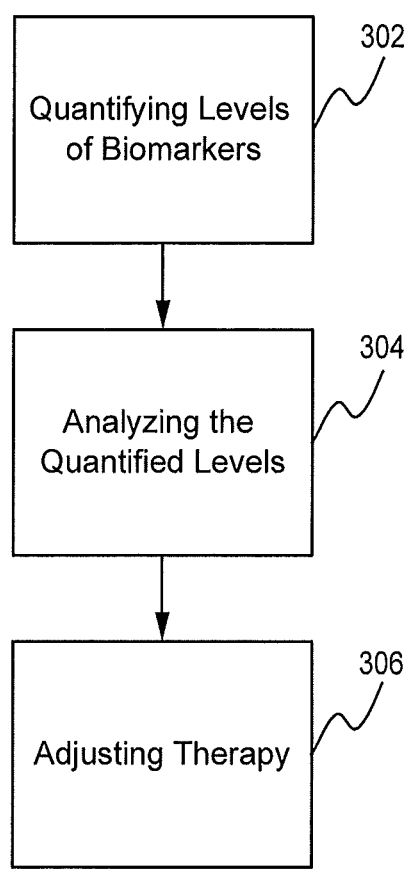
FIG. 3 is a flow chart of some steps of methods in accordance with various embodiments herein.

In some embodiments, a method of treating a patient is included. Referring now to FIG. 3, in some embodiments, methods herein can include quantifying levels of biomarkers 302, analyzing the quantified levels 304, and adjusting therapy being received by a patient 306, based at least in part on the analysis results. Adjusting therapy can include various steps. In some embodiments, adjusting therapy for the patient includes at least one selected from the group consisting of initiating the administration of CRT therapy to the patient with an implanted medical device and changing the parameters of CRT therapy administered to the patient. Exemplary parameters of CRT therapy can include, but are not limited to, A-V delay, V-V delay, stimulation vector, and the like. In some embodiments, adjusting therapy can be performed as part of a closed-loop process. In some embodiments, changes to the parameters of CRT therapy can be made by an implanted device automatically. In some embodiments, changes to the parameters of CRT therapy can be made by an external device and then programmed into an implanted device. In other embodiments, adjusting therapy can include suggesting changes in therapy to a clinician through an alert notice or other display on an external device.

In some embodiments, a method of treating a patient receiving CRT therapy is included. The method can include selecting a patient that is receiving CRT therapy, quantifying levels of one or more of a panel of biomarkers in a biological sample of the patient, analyzing the quantified levels to determine an expected response to CRT therapy, comparing the expected response to CRT therapy to the patient's actual response to CRT therapy, and adjusting parameters of the CRT therapy if the patient's actual response to CRT therapy is worse than the expected response to CRT therapy. Whether or not the response to CRT therapy is worse than the expected response can be determined subjectively by a clinician or can be objectively determined through techniques including analysis based on responses of comparison populations of patients. In some embodiments, whether heart failure is worse can be determined according to cardiac pump function, amount of fluid accumulation, activity/exercise tolerance, kidney and cerebral/cognitive function, amongst others. Again, exemplary parameters of CRT therapy can include, but are not limited to, A-V delay, V-V delay, stimulation vector, and the like.

In some embodiments, a method of monitoring a patient receiving CRT therapy is included herein. The method can include quantifying levels of one or more of a panel of biomarkers in a biological sample of the patient and analyzing the quantified levels to determine status of the patient. Analyzing the status of the patient can include classifying the patient into one of a set of possible status indicators. The set of possible status indicators can include one or more of improving condition, worsening condition, or maintaining status quo. In an embodiment, a method of monitoring a patient receiving CRT therapy includes quantifying levels of one or more of a panel of biomarkers in a biological sample of the patient, and analyzing the change in quantified levels over time to determine response to therapy changes or to monitor disease progression.

Figure 4:
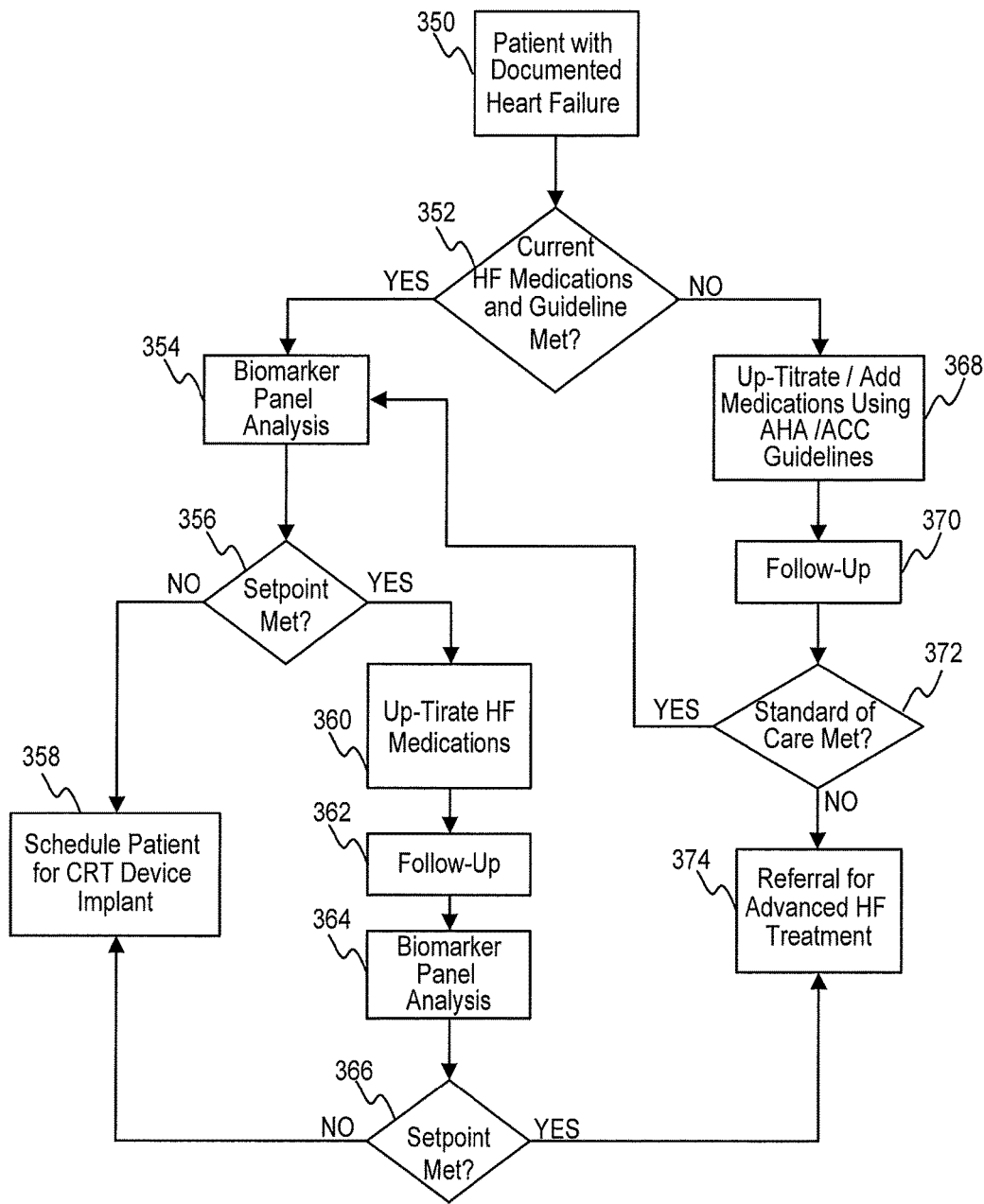
FIG. 4 is a flow chart of some steps of methods in accordance with various embodiments herein.

Referring now to FIG. 4, a flow chart of some steps of methods in accordance with various embodiments herein is shown. Specifically, FIG. 4 shows one example of a multivariate biomarker profiling and decision algorithm for aiding in the determination of whether cardiac resynchronization therapy (CRT) would be beneficial in patients with signs and symptoms of heart failure (HF). In some embodiments, patients are considered if they have signs and symptoms of systolic heart failure. Using the total biomarker panel or a subset of these biomarkers, a high level of prediction (for example, AUC >0.80 in some embodiments) can be achieved which will identify those patients with HF and the greatest probability of response. In some embodiments the biomarker panel can achieve an AUC >0.60. In some embodiments the biomarker panel can achieve an AUC >0.70. In some embodiments the biomarker panel can achieve an AUC >0.80. In the method (or algorithm) of FIG. 4 in operation 350, patients that have documented HF would be considered. The patients would then be evaluated in operation 352 to determine if they have been treated according to current American Heart Association/American College of Cardiology (AHA/ACC) guidelines. If they have, then in operation 354 biomarker panel analysis would be conducted. Then, in operation 356, it would be determined whether or not the biomarker profile for the patient is above the prediction set point limit based on the AUC (area under the curve in ROC analysis) of the biomarker profile as implemented. In some embodiments, the set point limit is a greater than 60 percent likelihood of non-response. In some embodiments, the set point limit is a greater than 70 percent likelihood of non-response. In some embodiments, the set point limit is a greater than 80 percent likelihood of non-response. In some embodiments, the set point limit is a greater than 90 percent likelihood of non-response. If the biomarker profile results are below the set point limit, then in operation 358 the patient can be referred for CRT device implant, or at least referred for further consideration of the same. However, if the biomarker profile results are above the set point limit (meaning for example, that there is a greater than 80% chance of non-response) then in operation 360 various steps can be taken including up-titrating heart failure medications. Then, after a time period, a follow-up 362 with the patient can be conducted. For example, a follow-up visit can take place after three months. Then, in operation 364 biomarker panel analysis can be repeated. Then, in operation 356, it can be again determined whether or not the biomarker profile for the patient is above the prediction set point limit. If the biomarker profile results are below the set point limit, then in operation 358 the patient can be referred for CRT device implant, or at least referred for further consideration of the same. However, if the biomarker profile results are above the set point limit then in operation 374 the patient can be referred for other advanced heart failure treatment.

Referring back to operation 352, if it is determined that the patient has not been treated according to current American Heart Association/American College of Cardiology (AHA/ACC) guidelines, then in operation 368 medications can be titrated and/or added or dropped in according to AHA and/or ACC guidelines. Then, after a time period, a follow-up 370 with the patient can be conducted. For example, a follow-up visit can take place after three months. Then in operation 372 it can be determined whether the standard of care is being met. If the answer is yes, then biomarker panel analysis can be performed according to operation 354. If not, then the patient can be referred for other advanced heart failure treatment in operation 374.

Figure 5:
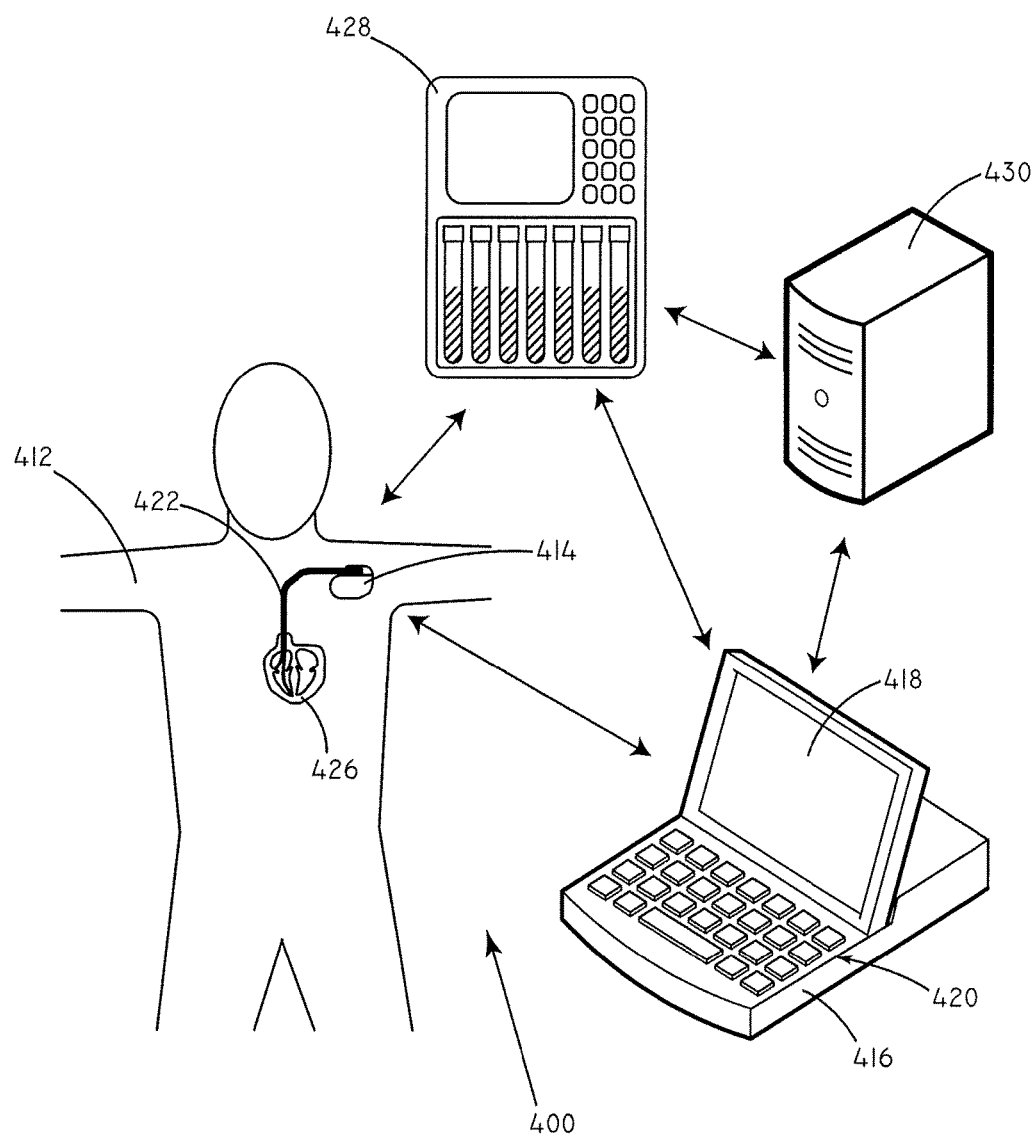
FIG. 5 is a schematic diagram of an exemplary system consistent with various embodiments herein.

Some embodiments can include systems and/or devices. However, it will be appreciated that embodiments related to biomarkers herein are not limited to implementation through devices or systems. FIG. 5 is a schematic view of some system 400 components, consistent with various embodiments herein. FIG. 5 schematically illustrates a biomarker diagnostic test being run and the values being communicated with a server as well as a device programmer (external medical device) and an implantable medical device. In some embodiments, the programmer can communicate with the device and based on the biomarker values reprogram the device settings as appropriate. Some embodiments can include all of the components shown in FIG. 5, while other embodiments include only some of the components. Data can pass from various specific components to other components within the system as indicated by the arrows. However, it will be appreciated that communication is not restricted to such pathways and that communication of data between devices can take place in various ways including automatically or through manual data input processes. The system 400 can include an implantable medical device 414. Methods described herein, or portions thereof, can be executed by the implantable medical device 414. The implantable medical device 414 can be disposed within a patient 412. The implantable medical device 414 can be of various types such as, for example, a pacemaker, a cardioverter-defibrillator, a cardiac resynchronization device, or the like. In some embodiments, the implantable medical device 414 is specifically a cardiac resynchronization device. One example of an implantable medical device is disclosed in commonly assigned U.S. Pat. No. 4,562,841, the content of which is herein incorporated by reference in its entirety. In some embodiments, the implantable medical device 414 can include one or more leads 422 disposed in or near the patient's heart 426. The leads can include a plurality of electrodes, such as ring and/or tip electrodes. In some embodiments, leads 422 can be positioned in both the left ventricle and the right ventricle of the heart.

The implantable medical device 414 can be in communication with an external medical device 416 (or device programmer). Methods described herein, or portions thereof, can be executed by the external medical device 416. In some embodiments, communication between the implantable medical device 414 and the external medical device 416 can be via inductive communication through a wand held on the outside of the patient 412 near the implantable medical device 414. However, in other embodiments, communication can be carried out via radiofrequency transmission, acoustically, or the like.

The external medical device 416 can include a video output device, such as a display screen 418 for displaying video output. In some embodiments, the external medical device 416 can be configured to process the gathered data. The external medical device 416 can also include a user input device 420, such as keys. The external medical system 416 can be for example, a programmer/recorder/monitor device, a computer, an advanced patient management system, or a personal digital assistant (PDA). Exemplary programmer/recorder/monitor devices include the Model 3120 Programmer, available from Boston Scientific Corporation, Natick, Mass.

In some embodiments the implantable medical device 414 can include one or more implantable sensors in order to gather data regarding the patient 412. By way of example, the medical device 414 can include an implantable sensor in order to sense concentrations of a predictive marker. In some embodiments, the implantable sensor can sense concentrations of CRP in vivo. Exemplary implantable sensors are described in U.S. Publ. Pat. Appl. No. 2007/0270675, the content of which is herein incorporated by reference in its entirety.

In some embodiments, concentrations of biomarkers can be measured using an in vitro assay. By way of example, in some embodiments, an external assay device 428 can be used to measure concentrations of a biomarker such as CRP. The patient 412 can provide an assayable quantity of blood or other bodily fluid to the external assay device 428 and the device can measure the amount of the biomarker present and then report back regarding concentration data either directly to the implantable medical device 414 or through the external medical device 416.

In some embodiments, the system 400 can include a server 430. The server 430 can be located remotely from other components of the system 400 but can be in communication such as through a network, such as a packet switched network. The server 430 can be in communication with one or more of the implantable medical device 414, the external medical device 416, and the external assay device 428, when such components are part of the system 400. The server 430 can include standard server components such as processor, memory, input/output interfaces, and the like. In some embodiments, the server 430 can further be in communication with a database (not shown). Methods described herein, or portions thereof, can be executed by the server 430.

Figure 6:
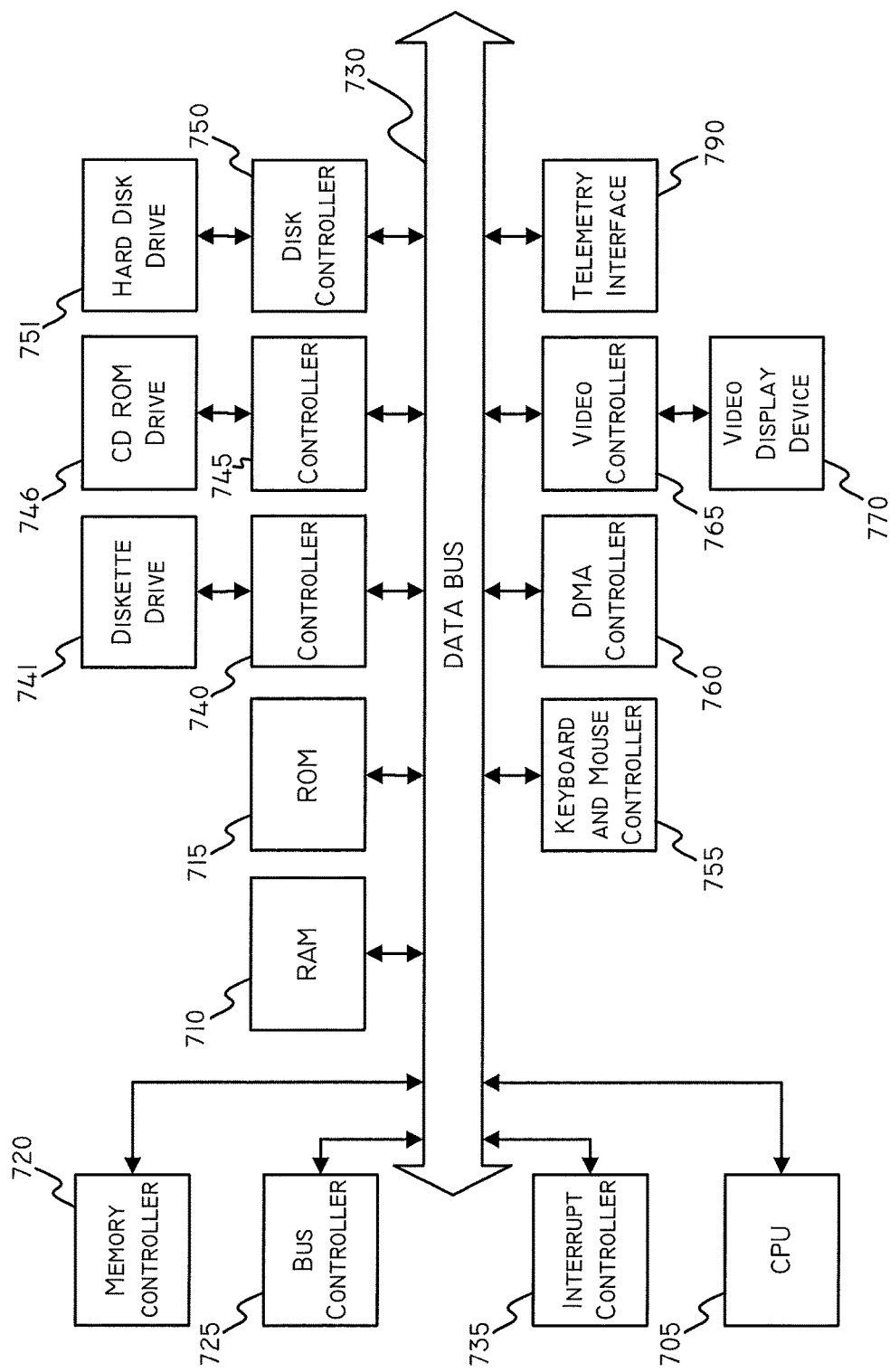
FIG. 6 is a schematic diagram of various components of an external device in accordance with some embodiments of the disclosure.

In some embodiments, one or more operations, methods described herein, or portions thereof can be executed by an external device. Exemplary external devices, such as programmer/recorder/monitors, can include components common to many computing devices. Referring now to FIG. 6, a diagram of various components is shown in accordance with some embodiments. The external system includes a central processing unit (CPU) 705 or processor, which may include a conventional microprocessor, random access memory (RAM) 710 for temporary storage of information, and read only memory (ROM) 715 for permanent storage of information. A memory controller 720 is provided for controlling system RAM 710. A bus controller 725 is provided for controlling data bus 730, and an interrupt controller 735 is used for receiving and processing various interrupt signals from the other system components.

In some embodiments mass storage can be provided by diskette drive 741, which is connected to bus 730 by controller 740, CD-ROM drive 746, which is connected to bus 730 by controller 745, and hard disk drive 751, which is connected to bus 730 by controller 750. User input to the programmer system may be provided by a number of devices. For example, a keyboard and mouse can connected to bus 730 by keyboard and mouse controller 755. DMA controller 760 is provided for performing direct memory access to system RAM 710. A visual display is generated by a video controller 765 or video output, which controls video display 770. The external system can also include a telemetry interface 790 or telemetry circuit which allows the external system to interface and exchange data with an implantable medical device or an external device. In some embodiments, the external system can include a network interface. The external programmer device can be configured to receive data regarding levels of one or more of a panel of biomarkers in a biological sample of a patient. This description of elements is only provided by way of example and it will be appreciated that some embodiments may lack various elements illustrated in FIG. 6. For example, some embodiments of external devices may lack a diskette drive 741.

Figure 7:
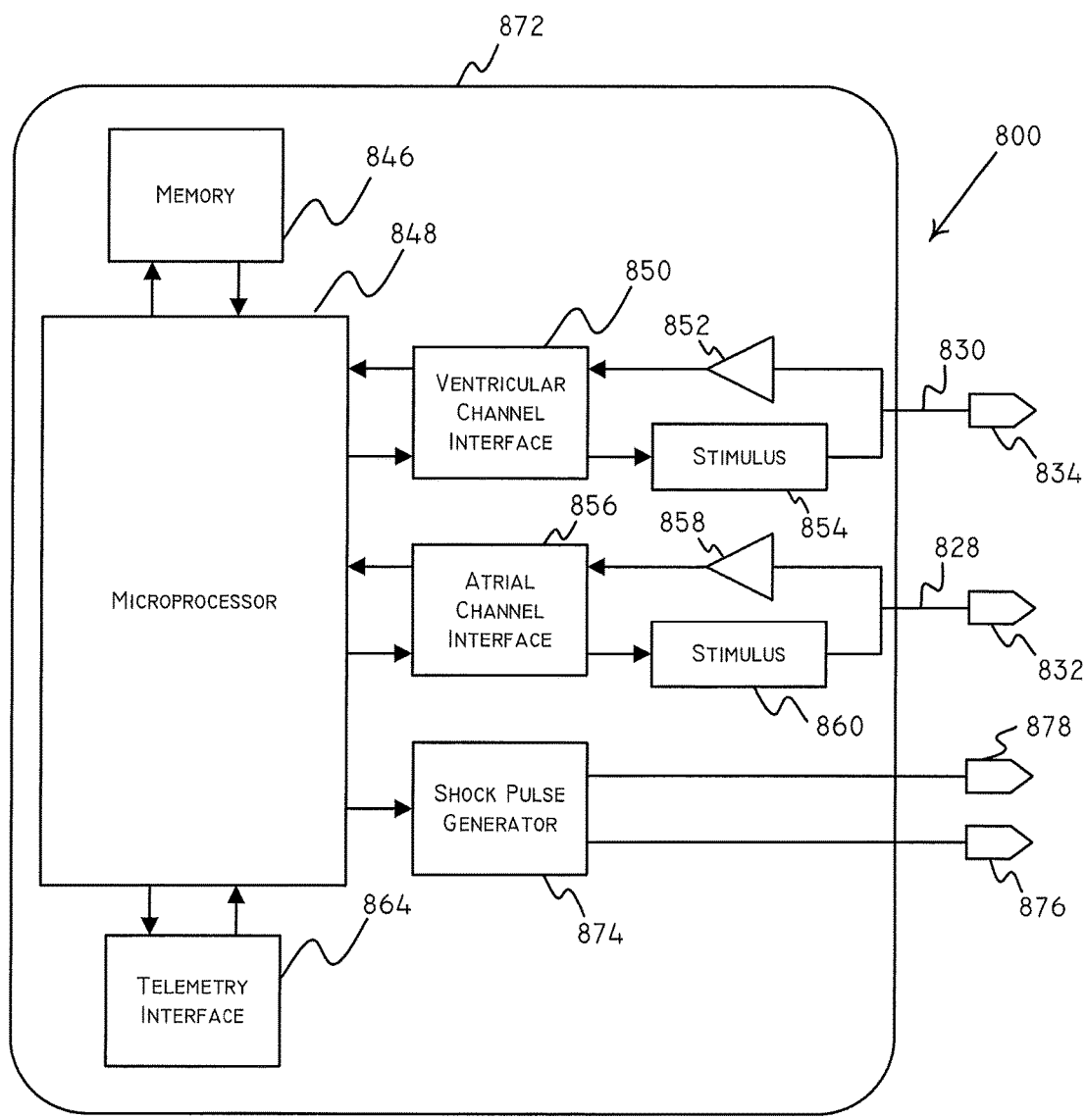
FIG. 7 is a schematic diagram of various components of an implantable device in accordance with some embodiments of the disclosure.

In some embodiments, one or more operations, methods described herein, or portions thereof can be executed by an implantable medical device. Referring now to FIG. 7, some components of an exemplary implantable device 800 are schematically illustrated. The implantable medical device 800 can include a controller module 872 coupled to one or more stimulation leads 830 and 828. The controller module 872 can include a microprocessor 848 (or processor) that communicates with a memory circuit (module) 846 via a bidirectional data bus. The memory circuit 846 can include ROM or RAM for program storage and ROM (such as EEPROM) or RAM for data storage. The controller module 872 can be configured to execute various operations such as processing of signals and execution of methods or portions thereof as described herein. For example, the controller module can be configured to process data regarding the levels of one or more of a panel of biomarkers. A telemetry interface 864 or communication circuit is also provided for communicating with an external unit, such as a programmer device or a patient management system. The communication circuit can be configured to receive data regarding levels of one or more of the panel of biomarkers.

The controller module 872 can include one or more ventricular sensing and pacing channels including sensing amplifier 852, output circuit 854, and a ventricular channel interface 850 which communicates bidirectionally with a port of microprocessor 848. Further, in some embodiments, additional elements may be included. The ventricular sensing and pacing channel can be in communication with stimulation lead 830 and electrode 834.

The controller module 872 can include one or more atrial sensing and pacing channels including sensing amplifier 858, output circuit 860, and an atrial channel interface 856 which communicates bidirectionally with a port of microprocessor 848. The atrial sensing and pacing channel can be in communication with stimulation lead 828 and electrode 832. For each channel, the same lead and electrode can be used for both sensing and pacing. The channel interfaces 850 and 856 can include analog-to-digital converters for digitizing sensing signal inputs from the sensing amplifiers and registers which can be written to by the microprocessor in order to output pulses, change the pacing pulse amplitude, and adjust the gain and threshold values for the sensing amplifiers. It will be appreciated that in some embodiments some of the elements of the controller module 872 shown in FIG. 7 may be omitted.

A shock pulse generator 874 can also be interfaced to the microprocessor for delivering defibrillation shocks to the heart via a separate pair of electrodes 876, 878. In some embodiments, electrodes 876 and 878 can be disposed along stimulation lead 830 and stimulation lead 828 respectively. In some embodiments, one or more of these components may be omitted. By way of example, if the implantable medical device is a pacemaker, then it may not include a shock pulse generator 874. Similarly, depending on the type of the device and its configuration, it may have a greater or lesser number of electrodes and channels.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this disclosure pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

EXAMPLES

Example 1: Biomarkers Relevant to CRT Response

Plasma was collected at baseline (during CRT evaluation, but prior to CRT implant), at 3 and 6 months post-CRT placement in a prospective fashion, from patients with heart failure enrolled in a trial (n=764). See Ellenbogen et al., *Primary results from the SmartDelay determined AV optimization: a comparison to other AV delay methods used in cardiac resynchronization therapy (SMART-AV) trial*. Circulation 2010; 122:2660-2668. The trial established a pre-specified endpoint of a reduction in LV end-systolic volume of 15 mL at 6 months post-CRT as a functional response and this definition was utilized in this biomarker profiling study. The initial goal of the trial was to compare 3 different modes of CRT atrioventricular (A-V) delay, which following randomization demonstrated relative equivalency for the primary endpoint, and therefore these patients were pooled for the present analysis.

Specifically, peripheral venous blood samples were collected from patients with heart failure who meet standard indications for CRT in the United States and Europe. Samples were collected by standard venipuncture in two (2) ethylenediamine tetraacetic acid (EDTA, 18 mg purple top) tubes (BD Vacutainer, 366643). Centrifugation was done at room temperature for 10 minutes at high speed (recommended to be ≥3,000 revolutions per minute (RPM) or >1300 g (relative centrifugal force=RCF=g)). The plasma from each blood sample tube was decanted into two separate and properly labeled polypropylene tubes. The plasma was kept on ice until it is transferred to a storage freezer. Plasma samples were frozen as soon as possible following centrifugation. The plasma sample were then stored in a −20° C. freezer until shipment. Samples were shipped to the analysis facility within 72 hours from enrolling centers.

90 candidate plasma proteins which spanned functional domains such as signaling, inflammation, myocyte/matrix structure for extraction efficiency, detection thresholds, and variability in referent non-device patients (n=25). This was followed by a validation phase of 18 candidate biomarkers in a second subset of the SMART-AV patient samples (n=25/25; responder/non-responder). For example, IFN-gamma was analyzed using an array (Millipore Cytokine Panel); sIL-2RA, and sTNF-RII were analyzed using an array (Millipore Cytokine Receptor Panel), sVCAM-1 was analyzed using an array (Millipore HCVD1 Panel); MMP-2 (LMP902; RnD Systems) and MMP-9 (LMP911; RnD Systems) were analyzed using an MMP Multiplex Array Panel (RnD Systems—Cat #LMP000); TIMP-1 was analyzed using TIMP Array Panel (Cat #LKT003; RnD Systems); CRP was analyzed using an ELISA assay (Cat #DCRP00; RnD Systems), BNP was analyzed using an ELISA assay (Cat #04-BI-20852, ALPCO Immunoassays); ST2 was analyzed using an ELISA assay (Cat #DST200; RnD Systems).

Using logistic regression and area under the curve (AUC), a final set of 12 biomarkers were analyzed by internally validated, robotic assisted, high sensitivity multiplex suspension array on the entire prospectively collected sample set (>2200 samples) where at 6 months, through independent review, 338 patients were defined as responders and 376 defined as non-responders.

The 12 biomarkers represented several domains: inflammatory (C-reactive protein: CRP, soluble glycoprotein 130: SGP-130, soluble interleukin-2 receptor: sIL-2R, soluble tumor necrosis factor receptor-II: sTNFR-II, interferon gamma: IFNg), bioactive (brain natriuretic peptide: BNP, soluble suppressor of tumorgenicity-2: sST2), and proteolytic (matrix metalloproteinase-2 and -9: MMP-2/-9, tissue inhibitors of MMP: TIMP-1, -2, -4). Significant differences in absolute values for several of these prospectively collected biomarkers occurred at baseline between those defined as responders and non-responders at 6 months, such as sST2 and sTNFR-II (31219±980 vs 35435±1120, and 8839±497 vs 9145±281 pg/mL, $p<0.05$, respectively).

Figure 8:
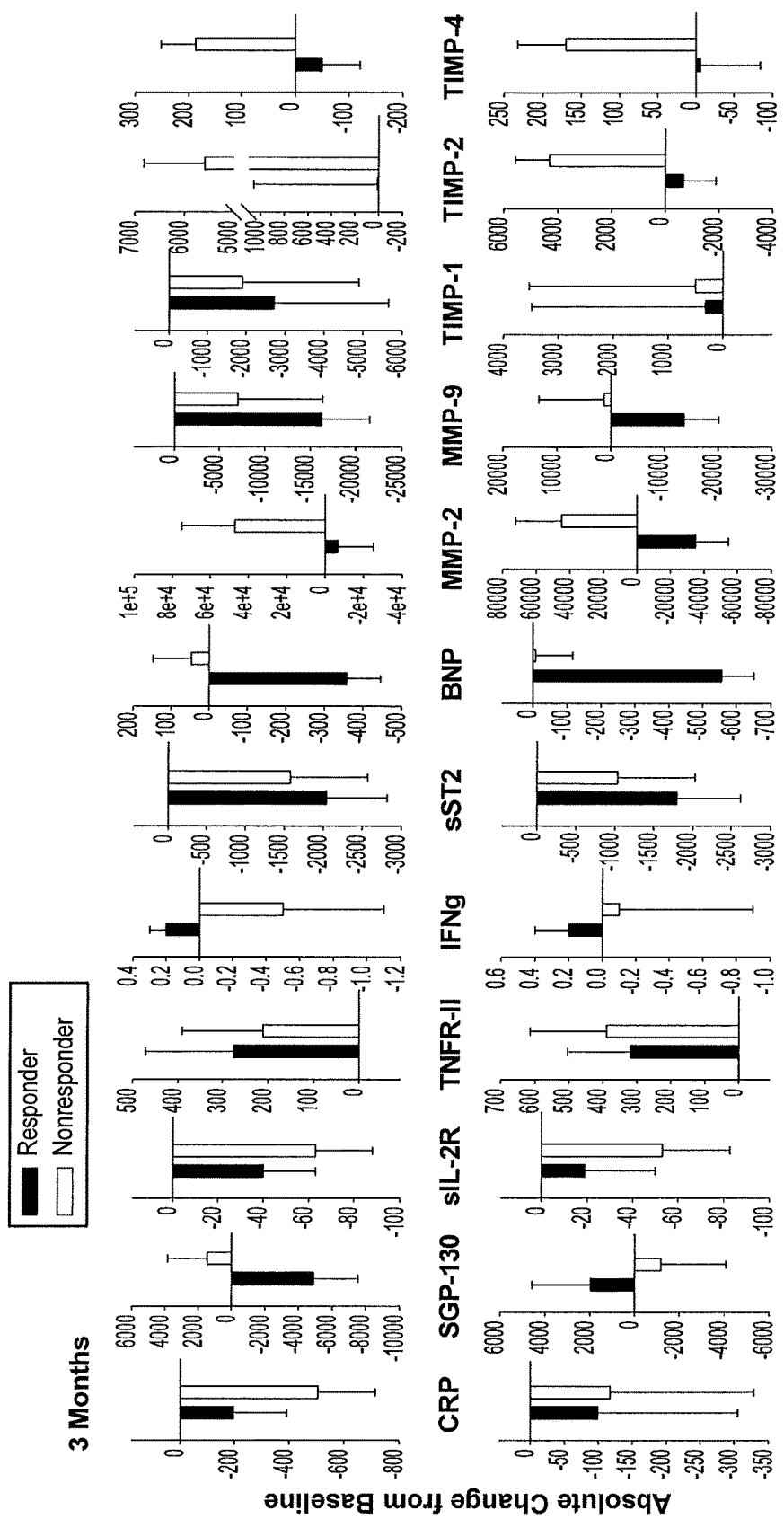
FIG. 8 is a graph showing absolute change from baseline at 3 and 6 months for CRT responders versus non-responders for 12 biomarkers.

More importantly, including the baseline measurements of all 12 biomarkers in a multivariable regression model yielded a significant AUC (0.60, $p<0.05$) for the prediction of CRT response at 6 months. In addition, a significant and differential biomarker profiles occurred as a function of time, between responders and non-responders to CRT (Figure). For example, at 3 months post-CRT significant and directional changes in BNP, MMP-2, TIMP-2 and TIMP-4 occurred between responders/non-responders ($p<0.05$), and a multivariable analysis of all 12 biomarkers at 3 months predicted 6 month response (AUC=0.64, $p<0.05$). FIG. 8 is a graph showing absolute change from baseline at 3 and 6 months for CRT responders versus non-responders for the 12 selected biomarkers. However, it will be appreciated that relative changes can also be considered in various embodiments.

The new and unique findings from this prospectively designed plasma profiling study include that a specific biomarker panel can successfully predict CRT response in patients with HF indicated for a device (NYHA Class III/IV, EF ≤35%, QRS duration >120 ms), as well as be utilized to monitor functional response following CRT. It will be appreciated, however, that embodiments herein are not limited to patients with that specific indication. Thus, plasma biomarker profiling can provide prognostic utility when evaluating patients with HF for CRT as well as an adjunctive diagnostic tool for monitoring functional response in the early period following CRT placement.

Multivariate logistic regression modeling was performed to assess positive responders (defined as change in LVESV (left ventricular end-systolic volume) from baseline ≤−15 ml) versus neutral/negative responders (defined as death within first 6 months or LVESV change from baseline >−15 ml). The following biomarker and clinical covariates included in the final multivariate model were selected using 10-fold cross validation methodology: ST2 (continuous variable), CRP (continuous variable), TIMP1 (continuous variable), TIMP2 (continuous variable), LVESV at baseline (continuous variable), age at baseline (continuous variable), sex (binary variable), systolic blood pressure at baseline (continuous variable), QRS duration at baseline (continuous variable), PR interval at baseline (continuous variable), ischemic status at baseline (binary variable), ACE (angiotensin-converting enzyme inhibitors)/ARB (angiotensin II receptor blockers) use at baseline (binary variable). Area under the curve (AUC) obtained via cross-validation for the final set of covariates equaled 0.731; AUC obtained by fitting the model on the entire dataset equaled 0.754.

Multivariate logistic regression modeling was performed to assess negative responders (defined as death within first 6 months or LVESV change from baseline ≥20 ml) versus positive/neutral responders (defined as LVESV change from baseline <20 ml). The following biomarker and clinical covariates included in the final multivariate model were selected using 10-fold cross validation methodology: CRP (continuous variable), BNP (continuous variable), LVESV at baseline (continuous variable), age at baseline (continuous variable), sex (binary variable), systolic blood pressure at baseline (continuous variable), presence of left bundle branch block at baseline (binary variable), renal disease at baseline (binary variable), ischemic status at baseline (binary variable), beta blocker use at baseline (binary variable). Area under the curve (AUC) obtained via cross-validation for the final set of covariates equaled 0.676; AUC obtained by fitting the model on the entire dataset equaled 0.715.

Multivariate logistic regression modeling was performed to assess positive responders (defined as change in LVESV from baseline ≤−15 ml) versus negative responders (defined as death within first 6 months or LVESV change from baseline ≥20 ml). The following biomarker and clinical covariates included in the final multivariate model were selected using 10-fold cross validation methodology: CRP (continuous variable), BNP (continuous variable), LVESV at baseline (continuous variable), age at baseline (continuous variable), sex (binary variable), systolic blood pressure at baseline (continuous variable), QRS duration at baseline (continuous variable), PR interval at baseline (continuous variable), ischemic status at baseline (binary variable), beta blocker use at baseline (binary variable), ACE/ARB use at baseline (binary variable). Area under the curve (AUC) obtained via cross-validation for the final set of covariates equaled 0.739; AUC obtained by fitting the model on the entire dataset equaled 0.765.

Multivariate cumulative logistic regression modeling was performed to assess response as a three level outcome: positive responders (defined as change in LVESV from baseline ≤−15 ml), neutral responders (defined as LVESV change from baseline >−15 ml and <20 ml), and negative responders (defined as death within first 6 months or LVESV change from baseline ≥20 ml). The following biomarker and clinical covariates included in the final multivariate model were selected using 10-fold cross validation methodology: BNP (continuous variable), CRP (continuous variable), TNFR-II (continuous variable), LVESV at baseline (continuous variable), age at baseline (continuous variable), sex (binary variable), systolic blood pressure at baseline (continuous variable), QRS duration at baseline (continuous variable), presence of left bundle branch block at baseline (binary variable), ischemic status at baseline (binary variable), renal disease at baseline (binary variable). Area under the curve (AUC) obtained via cross-validation for the final set of covariates equaled 0.681; AUC obtained by fitting the model on the entire dataset equaled 0.696.

Additional Embodiments

In an embodiment, an assay kit is included. The assay kit can include probes to quantify levels of one or more of a panel of biomarkers in a biological sample of a patient; wherein the panel of biomarkers includes at least two selected from the group consisting of CRP, SGP-130, sIL-2R, sTNFR-II, IFNg, BNP, sST2, MMP-2, MMP-9, TIMP-1, TIMP-2, and TIMP-4. In an embodiment, the panel of biomarkers includes at least three selected from the group consisting of CRP, SGP-130, sIL-2R, sTNFR-II, IFNg, BNP, sST2, MMP-2, MMP-9, TIMP-1, TIMP-2, and TIMP-4. In an embodiment, the panel of biomarkers includes at least four selected from the group consisting of CRP, SGP-130, sIL-2R, sTNFR-II, IFNg, BNP, sST2, MMP-2, MMP-9, TIMP-1, TIMP-2, and TIMP-4.

In an embodiment, an implantable medical device is included. The implantable medical device can include a processor, and a communication circuit operably connected to the processor. The communication circuit can be configured to receive data regarding levels of one or more of a panel of biomarkers in a biological sample of a patient; the panel of biomarkers including at least one selected from the group consisting of CRP, SGP-130, sIL-2R, sTNFR-II, IFNg, BNP, sST2, MMP-2, MMP-9, TIMP-1, TIMP-2, and TIMP-4. The device can further be configured to modulate therapy based on the data regarding levels of the one or more of the panel of biomarkers. In an embodiment, the panel of biomarkers includes at least three selected from the group consisting of CRP, SGP-130, sIL-2R, sTNFR-II, IFNg, BNP, sST2, MMP-2, MMP-9, TIMP-1, TIMP-2, and TIMP-4. In an embodiment, the panel of biomarkers includes at least four selected from the group consisting of CRP, SGP-130, sIL-2R, sTNFR-II, IFNg, BNP, sST2, MMP-2, MMP-9, TIMP-1, TIMP-2, and TIMP-4. The implantable medical device can be configured to change the parameters of CRT therapy administered to the patient based on the data regarding the levels of one or more of the panel of biomarkers.

In an embodiment, a medical system is included. The medical system can include an external programmer device and an implantable medical device. The implantable medical device can be configured to communicate with the programmer through a telemetry interface. The external programmer device can be configured to receive data regarding levels of one or more of a panel of biomarkers in a biological sample of a patient; the panel of biomarkers including at least one selected from the group consisting of CRP, SGP-130, sIL-2R, sTNFR-II, IFNg, BNP, sST2, MMP-2, MMP-9, TIMP-1, TIMP-2, and TIMP-4. The external programmer device can be configured to process the data regarding the levels of one or more of the panel of biomarkers. The external programmer device can be configured to send programming instructions regarding CRT therapy to the implantable device based on the data regarding the levels of one or more of the panel of biomarkers.

What is claimed is:

1. A method of treating a patient with CRT therapy comprising:
   selecting a patient exhibiting heart failure symptoms and lacking a CRT device;
   quantifying levels of a panel of biomarkers in a biological sample of the patient;
   analyzing the quantified levels to determine response to CRT therapy with an external medical device comprising a microprocessor, wherein the microprocessor
      analyzes the quantified levels comprising comparing quantified levels to threshold levels to determine likelihood of response to CRT therapy; and
      places the patient into one of a set of categories using the quantified levels, the set of categories including at least one of CRT therapy responders, CRT therapy non-responders, and indeterminate response;
   referring the patient for CRT device implant if the patient is in the CRT therapy responders category;
   the panel of biomarkers comprising at least CRP, sST2, TIMP-1, and TIMP-2.

2. The method of claim 1, further comprising implanting a CRT device if the patient is in the CRT therapy responders category.

3. The method of claim 1, the panel of biomarkers further including at least one additional biomarker selected from the group consisting of SGP-130, sIL-2R, sTNFR-II, IFNg, BNP, MMP-2, MMP-9, and TIMP-4.

4. The method of claim 1, further comprising selecting a patient that is not indicated for CRT therapy.

5. The method of claim 1, the heart failure symptoms comprising one or more of cardiac pump function, fluid accumulation, activity/exercise tolerance, kidney and cerebral/cognitive function.

6. A method of treating a patient that is receiving CRT therapy:
   selecting a patient that is receiving CRT therapy;
   quantifying levels of a panel of biomarkers in a biological sample of the patient;
   analyzing the quantified levels to determine an expected response to CRT therapy with an external medical device comprising a microprocessor, wherein the microprocessor
   compares the expected response to CRT therapy to the patient's actual response to CRT therapy; and
   adjusts parameters of the CRT therapy if the patient's actual response to CRT therapy is worse than the expected response to CRT therapy;
   the panel of biomarkers comprising at least CRP, sST2, TIMP-1, and TIMP-2.

7. The method of claim 6, further comprising analyzing the change in quantified levels over time to perform one or more selected from the group consisting of analyzing response to therapy changes and monitoring disease progression.

8. The method of claim 6, the parameters of the CRT therapy comprising at least one of A-V delay, V-V delay, and stimulation vector.

9. The method of claim 6, the panel of biomarkers further including at least one additional biomarker selected from the group consisting of SGP-130, sIL-2R, sTNFR-II, IFNg, BNP, MMP-2, MMP-9, and TIMP-4.

10. The method of claim 6, further comprising providing an alert notice to a clinician regarding changes in parameters of CRT therapy.

11. A method of treating a patient with CRT therapy comprising:
    selecting a patient exhibiting heart failure symptoms and lacking a CRT device;
    quantifying levels of a panel of biomarkers in a biological sample of the patient;
    analyzing the quantified levels to determine response to CRT therapy with an external medical device comprising a microprocessor, wherein the microprocessor
       analyzes the quantified levels comprising comparing quantified levels to threshold levels to determine likelihood of response to CRT therapy; and
       places the patient into one of a set of categories using the quantified levels, the set of categories including at least one of CRT therapy responders, CRT therapy non-responders, and indeterminate response;

treating the patient with a CRT device if the patient is in the CRT therapy responders category;
the panel of biomarkers comprising at least CRP, sST2, TIMP-1, and TIMP-2.

* * * * *